(12) United States Patent
Kim et al.

(10) Patent No.: US 10,556,232 B2
(45) Date of Patent: Feb. 11, 2020

(54) FLUID ANALYSIS CARTRIDGE AND FLUID ANALYSIS CARTRIDGE ASSEMBLY HAVING THE SAME

(71) Applicant: SAMSUNG ELECTRONICS CO., LTD., Suwon-si (KR)

(72) Inventors: Hong-Geun Kim, Suwon-si (KR); Seung Hyun Kim, Anyang-si (KR); Sung Ha Park, Suwon-si (KR); Ji Young Park, Seoul (KR); Kyung-Mi Song, Suwon-si (KR); Dae Sun Lee, Hwaseong-si (KR); Jong Gun Lee, Yongin-si (KR); Jong Yup Choi, Suwon-si (KR); Yu Kyung Tak, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 326 days.

(21) Appl. No.: 15/613,504

(22) Filed: Jun. 5, 2017

(65) Prior Publication Data
US 2018/0221866 A1    Aug. 9, 2018

(30) Foreign Application Priority Data
Feb. 6, 2017   (KR) .................. 10-2017-0016004

(51) Int. Cl.
*B01L 3/00* (2006.01)
*G01N 33/49* (2006.01)

(52) U.S. Cl.
CPC ....... *B01L 3/5023* (2013.01); *B01L 3/502715* (2013.01); *B01L 3/502746* (2013.01);
(Continued)

(58) Field of Classification Search
CPC ............ B01L 3/5023; B01L 3/502746; B01L 3/502715; B01L 2400/0481;
(Continued)

(56) References Cited

U.S. PATENT DOCUMENTS

| 5,638,828 A | 6/1997 | Lauks et al. |
| 2003/0064526 A1 | 4/2003 | Niedbala et al. |

(Continued)

FOREIGN PATENT DOCUMENTS

| CN | 202204706 U | 4/2012 |
| EP | 1 445 020 A1 | 8/2004 |

(Continued)

OTHER PUBLICATIONS

International Search Report (PCT/ISA/210), issued by International Searching Authority in corresponding International Application No. PCT/KR2017/006192, dated Nov. 6, 2017.
(Continued)

*Primary Examiner* — Dennis White
(74) *Attorney, Agent, or Firm* — Sughrue Mion, PLLC

(57) ABSTRACT

A fluid analysis cartridge with improved test reliability and an associated fluid analysis cartridge assembly are disclosed herein. A fluid analysis cartridge assembly includes a sample collecting member having a sample collecting chamber and a fluid analysis cartridge configured to be connected to the sample collecting member. The fluid analysis cartridge includes a sample receiving chamber configured to receive a sample collected by the sample collecting member and at least one hole arranged on one side of the sample receiving chamber and opened by connection of the sample collecting member to the fluid analysis cartridge to the at least one hole. The sample receiving chamber stores a buffer solution to be mixed with the sample.

17 Claims, 12 Drawing Sheets

(52) U.S. Cl.
CPC .. *G01N 33/4905* (2013.01); *B01L 2300/0816* (2013.01); *B01L 2300/0867* (2013.01)

(58) Field of Classification Search
CPC ......... B01L 2300/123; B01L 2300/087; B01L 2300/0672; B01L 2300/044; B01L 2200/10; B01L 2200/0689; B01L 2200/0621; B01L 2200/027; B01L 2300/0867; B01L 2300/0816; B01L 2400/0683; G01N 35/00069; G01N 33/4905; G01N 2001/383
See application file for complete search history.

(56) References Cited

U.S. PATENT DOCUMENTS

| | | |
|---|---|---|
| 2004/0191124 A1 | 9/2004 | Noetzel et al. |
| 2007/0020612 A1 | 1/2007 | Van Agthoven et al. |
| 2007/0154351 A1 | 7/2007 | Bae et al. |
| 2009/0221431 A1 | 9/2009 | Yoo |
| 2009/0246814 A1 | 10/2009 | Kobold et al. |
| 2010/0167420 A1 | 7/2010 | Mpock |
| 2010/0255460 A1 | 10/2010 | Kriz et al. |
| 2010/0286557 A1 | 11/2010 | Choi et al. |
| 2011/0150705 A1 | 6/2011 | Doyle et al. |
| 2011/0301186 A1 | 12/2011 | Levy |
| 2015/0093771 A1 | 4/2015 | Griss et al. |
| 2015/0219536 A1 | 8/2015 | Hoder et al. |
| 2015/0300957 A1 | 10/2015 | Salsman |
| 2016/0151776 A1 | 6/2016 | Cremien et al. |
| 2016/0220160 A1 | 8/2016 | Ivosevic et al. |

FOREIGN PATENT DOCUMENTS

| | | | |
|---|---|---|---|
| EP | 2 222 229 | 5/2009 | |
| KR | 1020150133774 A | 11/2015 | |
| KR | 1020160018201 A | 2/2016 | |
| WO | 2017015172 A1 | 1/2017 | |
| WO | WO-2017015172 A1 * | 1/2017 | ....... G01N 33/54366 |

OTHER PUBLICATIONS

Communication dated Jan. 17, 2018, from the European Patent Office in counterpart European Application No. 17179292.2.
Communication dated Mar. 14, 2019 issued by the European Intellectual Property Office in counterpart European Application No. 17 179 292.2.
Communication dated Jul. 20, 2018, from the European Patent Office in counterpart European Application No. 17179292.2.

* cited by examiner

FLUID ANALYSIS CARTRIDGE AND FLUID ANALYSIS CARTRIDGE ASSEMBLY HAVING THE SAME

CROSS-REFERENCE TO RELATED APPLICATION

This application claims priority to and the benefit of Korean Patent Application No. 10-2017-0016004, filed on Feb. 6, 2017, the disclosure of which is incorporated herein by reference in its entirety.

BACKGROUND

1. Technical Field

The present disclosure relates to a fluid analysis cartridge and fluid analysis cartridge assembly having the same, and more particularly, to a fluid analysis cartridge with an improved structure to increase test reliability and fluid analysis cartridge assembly having the same.

2. Discussion of Related Art

A variety of applications, such as environmental monitoring, food testing, medical diagnosis, and other technical applications, require the use of an apparatus and/or method for analyzing a fluid sample. In the past, to perform a test of a sample according to a predetermined protocol, a skilled tester would have to manually conduct many different steps, such as injection of a reagent, mixing, separation and migration, reaction, centrifugalization, and possibly other steps multiple times. The tester might accidentally cause an error while conducting one or more of these steps.

To address this problem, a compact automated system that can quickly analyze a test material has been developed. If the structure and function of a portable fluid analysis cartridge capable of promptly analyzing a fluid sample at any place are enhanced, the fluid analysis cartridge may have more diverse functions in more areas. With an enhanced fluid analysis cartridge, non-experts may also easily conduct a test.

In the related art, a general procedure of collecting and analyzing an object's (i.e., a patient's) blood for the purpose of medical diagnosis is as follows. After a blood sample is collected from the object, the blood sample is injected into a tube. A tester then shakes the tube to evenly mix the blood contained therein. After sufficiently shaking the tube, the tester transfers a certain amount of blood from the tube onto a fluid analysis cartridge, and then inserts the fluid analysis cartridge into a fluid analysis device for analysis of the blood. The procedure for collecting and analyzing blood from an object should go through such multiple steps, and there is a risk that the blood could be dispersed, spilled, or contaminated when the tester drops a certain amount of blood onto the fluid analysis cartridge.

SUMMARY

The present disclosure provides a fluid analysis cartridge and a fluid analysis cartridge assembly that can simplify and/or improve a procedure of collecting and analyzing a sample from an object.

The present disclosure also provides a fluid analysis cartridge and a fluid analysis cartridge assembly that operate to minimize variations between users.

In accordance with one aspect of the present disclosure, a fluid analysis cartridge assembly includes a sample collecting member having a sample collecting chamber and a fluid analysis cartridge configured to be connected to the sample collecting member. The fluid analysis cartridge includes a sample receiving chamber configured to receive a sample contained in the sample collecting member and at least one hole located on one side of the sample receiver, the hole being opened by connection of the sample collecting member. The sample receiving chamber stores a buffer solution to be mixed with the sample.

The fluid analysis cartridge further includes at least one patch attached to the sample receiving chamber to cover the at least one hole.

The sample receiving chamber further includes a second hole on the bottom surface of the sample receiving chamber, and a second patch attached to the sample receiving chamber to cover the second hole.

The fluid analysis cartridge further includes a housing with the sample receiving chamber and the at least one hole arranged therein and a test chamber coupled to the housing for receiving a reagent to react with a sample input to the sample receiver. The sample receiving chamber further includes a second hole formed on a bottom surface of the sample receiving chamber so that the sample is provided to the test chamber.

The at least one patch further includes a second patch attached to the bottom surface of the sample receiver to cover the second hole. The second hole is opened when the second patch is pressed by the sample collector inserted to the first hole.

The sample receiving chamber further includes a second patch. The second patch includes an attachment part attached on the bottom surface of the sample receiving chamber to cover the second hole and a pressed part formed to extend from the attachment part to be pressed by the sample collecting member.

The pressed part is formed to extend from the attachment part so as to be inclined upward in a direction of depth D of the sample receiver with respect to the attachment part.

The fluid analysis cartridge further includes a housing with the sample receiving chamber and the at least one hole arranged therein and a sealing member coupled to the housing to cover an opened side of the sample receiving chamber.

In accordance with one aspect of the present disclosure, the fluid analysis cartridge assembly further includes a pressing member configured to press the sealing member. The sealing member has a flexible material to be pressed by the pressing member.

The fluid analysis cartridge further includes a test chamber coupled to the housing for receiving a reagent to react with a sample input to the sample receiver. The sample and buffer solution received in the sample receiving chamber flow to the test chamber according to a pressure difference between the sample receiving chamber and the test chamber occurring as the pressing member presses the sealing member.

The fluid analysis cartridge further includes a housing with the sample receiving chamber and the at least one hole arranged therein and a housing cover integrally formed with the housing and having a plurality of openings for air ventilation.

In accordance with one aspect of the present disclosure, a fluid analysis cartridge includes a housing, a sample receiving chamber arranged in the housing to receive a sample and at least one hole formed in the sample receiving chamber. The sample receiving chamber stores a buffer solution to be mixed with the sample.

In accordance with one aspect of the present disclosure, the fluid analysis cartridge further include a test chamber coupled to the housing for receiving a reagent to react with a sample input to the sample receiving chamber.

In accordance with one aspect of the present disclosure, the fluid analysis cartridge further include at least one patch attached to the sample receiving chamber to cover the at least one hole.

The sample receiving chamber includes a bottom surface and an inclined surface formed to extend from the bottom surface. The at least one hole is formed in the inclined surface for the sample collector to be inserted thereto. The at least one patch is attached to the inclined surface to be penetrated by the sample collector inserted to the first hole.

The sample receiving chamber further includes a second hole formed in the bottom surface to be linked with the test chamber. The sample receiving chamber further includes a second patch attached to the bottom surface to open the second hole by being pressed by the sample collector inserted to the first hole.

The second patch includes an attachment part attached on the bottom surface to cover the second hole and a pressed part formed to extend from the attachment part to be pressed by the sample collecting chamber toward the test chamber.

The sample receiving chamber is formed with one side open. In accordance with one aspect of the present disclosure, the fluid analysis cartridge further includes a sealing member coupled to the housing to cover the open side of the sample receiver and having a flexible material.

In accordance with one aspect of the present disclosure, a fluid analysis cartridge assembly includes a sample collecting member having a sample collecting chamber and a fluid analysis cartridge including a sample receiving chamber arranged to receive a sample collected by the sample collecting member, a first hole formed in the sample receiver for the sample collector to be inserted thereto, and a second hole opened by a portion of the sample collecting member inserted to the first hole.

The sample receiving chamber includes a patch. The patch includes an attachment part attached on the sample receiving chamber to cover the second hole and a pressed part formed to extend from the attachment part so as to be inclined with respect to the attachment part, and to be pressed by the sample collector in a direction of connection C of the sample collector against the first hole.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings

DETAILED DESCRIPTION OF EXEMPLARY EMBODIMENTS

Figure 1:
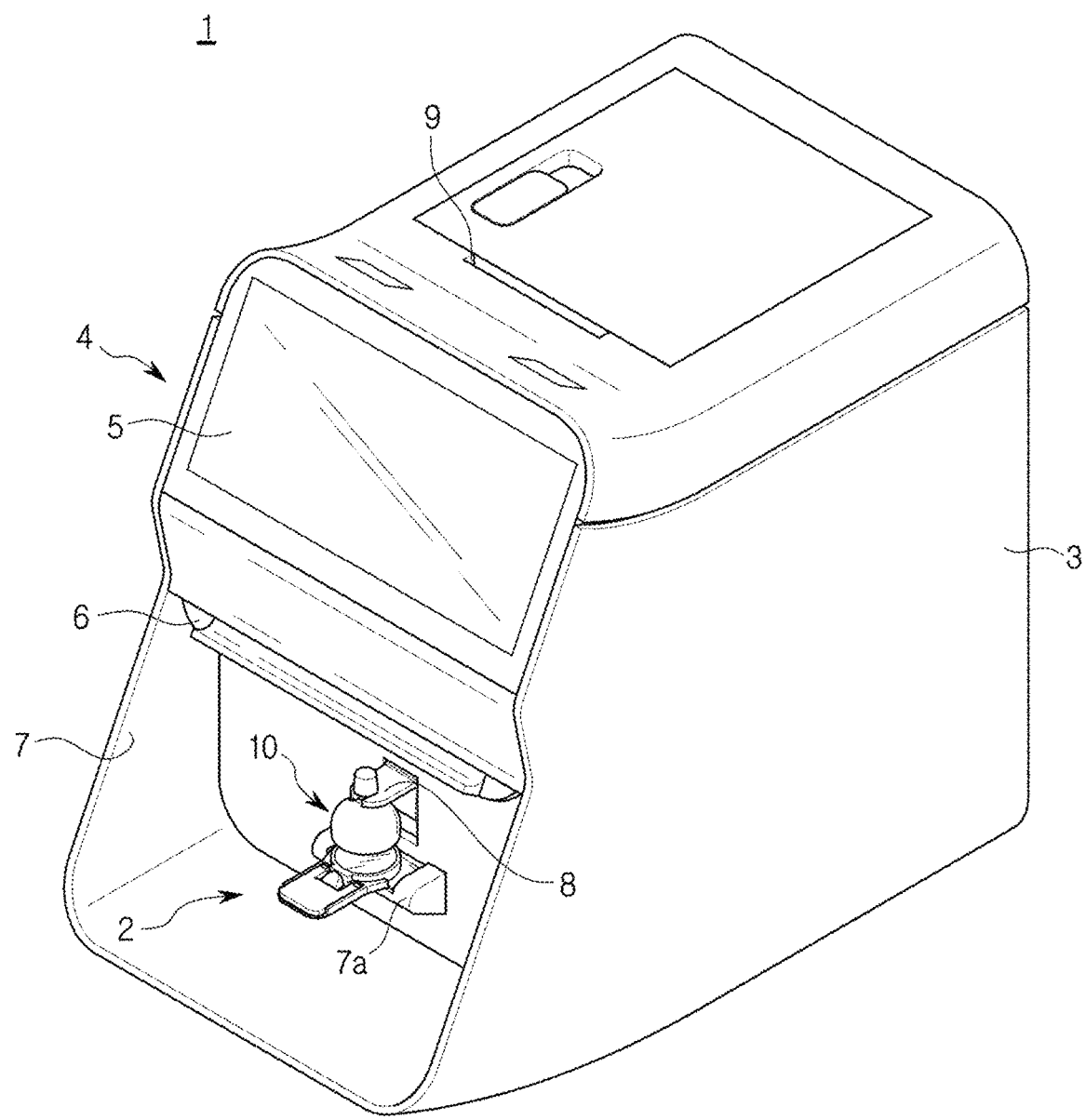
FIG. 1 is a perspective view of the appearance of a flow analysis device, according to an embodiment of the present disclosure.

Reference will now be made in detail to exemplary embodiments, which are illustrated in the accompanying drawings, wherein like reference numerals refer to the like elements throughout. The terms "front", "rear", "upper", "lower", "top", and "bottom" as herein used are defined with respect to the drawings, but the terms may not restrict the shape and position of the respective components.

FIG. 1 is a perspective view of a fluid analysis device, according to an exemplary embodiment of the present disclosure.

Referring to FIG. 1, a fluid analysis device 1 may include a casing 3 that forms an external structure, and a door module 4 equipped at the front of the casing 3.

The door module 4 may include a display 5, a door 6, and a door frame 7. The display 5 and door 6 may be arranged at the front of the door frame 7. The display 5 may be located on top of the door 6. The door 6 may be a sliding one, which may be positioned behind the display 5 as it slides open.

The display 5 may display information about sample analysis content, sample analysis operation state, testing times, testing status, error messages, or other pertinent testing information. The door frame 7 may have a mounting member 7a on which a fluid analysis cartridge 20 receiving a fluid sample is mounted. The user may slide the door 6 open upward, mount the fluid analysis cartridge 20 on the mounting member 7a, slide the door 6 closed downward, and then perform an analysis. In other embodiments, the door could slide downward or from side to side.

The fluid analysis device 1 may further include a fluid analysis cartridge assembly 2. As will be described below, the fluid analysis cartridge assembly 2 may include a sample collecting member 40 and the fluid analysis cartridge 20.

The fluid analysis cartridge assembly 2 may be attached to, or detached from, the fluid analysis device 1.

A fluid sample is injected into the fluid analysis cartridge 20, and the fluid sample reacts on a reagent in a test unit 30 (also referred to as a test chamber). The fluid analysis assembly 2 may be inserted into or onto the mounting member 7a, and a pressing member 10 may press the fluid analysis cartridge 20 for the fluid sample in the fluid analysis cartridge 20 to be input to the test unit 30. The pressing member 10 may be combined with a lever 8 of the fluid analysis device 1.

The fluid analysis device 1 may further include an output port 9 for outputting the test result in a printed format apart from the display 5. A printer (not shown) for printing the test result may be located inside the fluid analysis device 1.

The fluid analysis device 1 may further include the pressing member 10 arranged to press a sample receiver 22 (also referred to as a sample receiving chamber). The pressing member 10 may press the sample receiver 22 such that the sample receiver is closed. The pressing member 10 may be combined with the lever 8, and may move up or down together with the lever 8.

The pressing member 10 may be formed to have at least one of elastic material and soft material. For example, the pressing member 10 may be formed of a rubber material or a plastic material.

Figure 2:
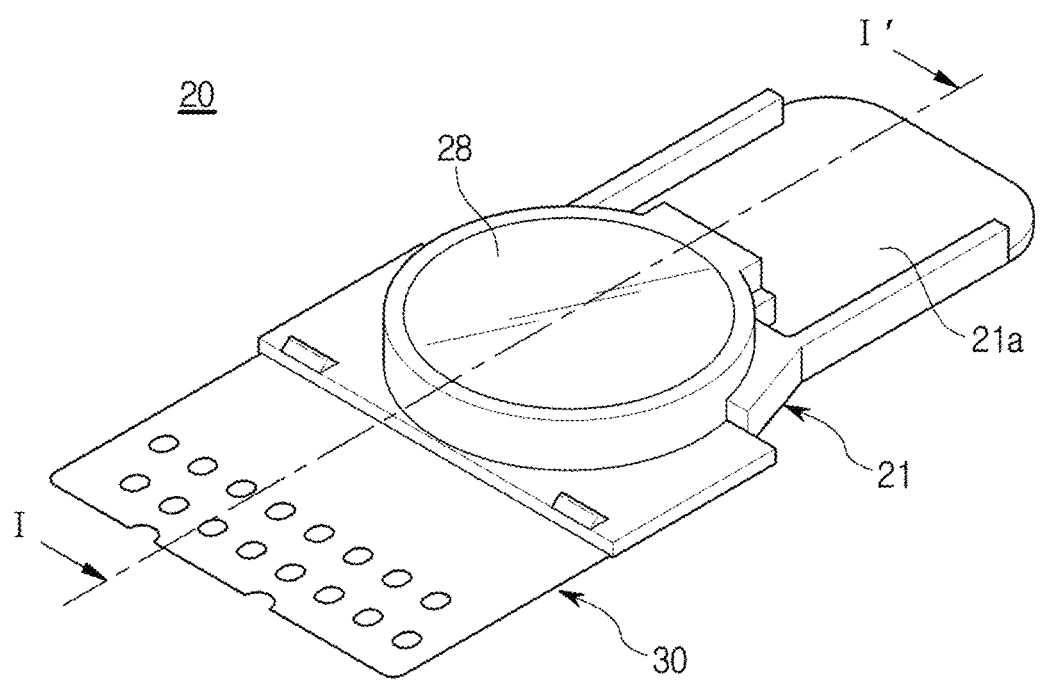
FIG. 2 is a perspective view of a fluid analysis cartridge, according to an embodiment of the present disclosure.
Figure 3:
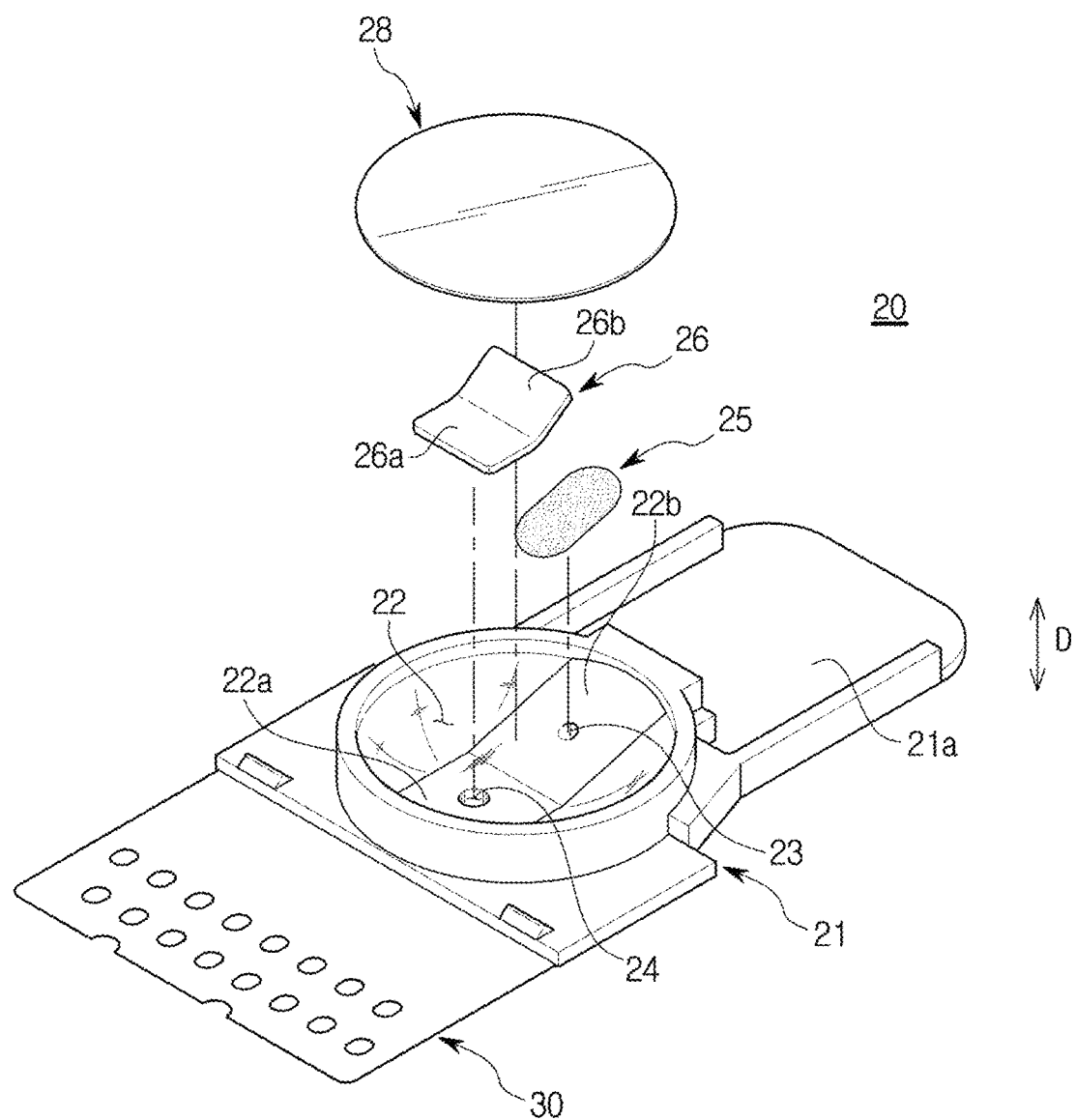
FIG. 3 is an exploded view of a fluid analysis cartridge, according to an embodiment of the present disclosure.
Figure 4:
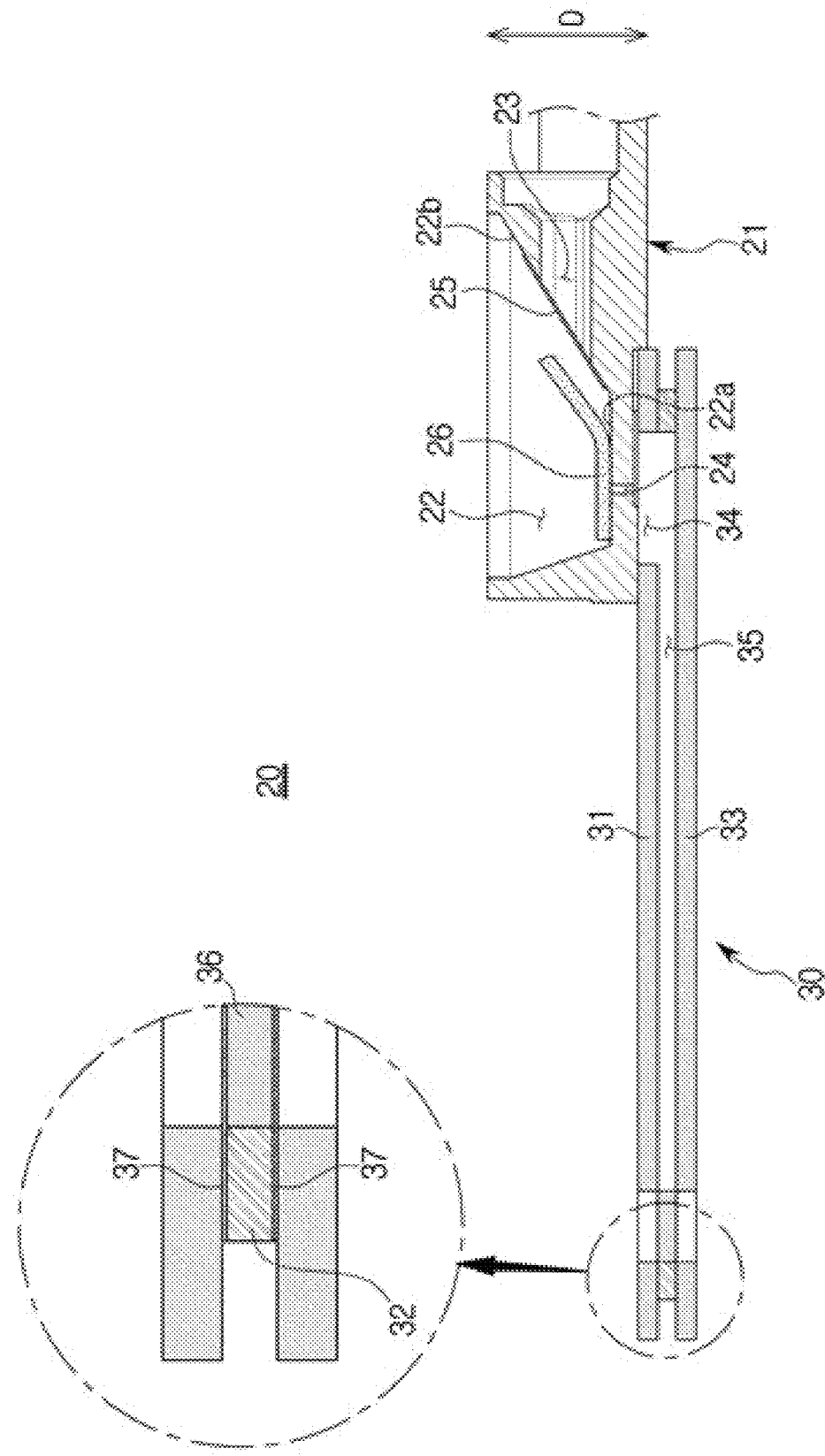
FIG. 4 is a cross-sectional view of a fluid analysis cartridge cut along line I-I' of FIG. 2.

FIG. 2 is a perspective view of a fluid analysis cartridge, according to an embodiment of the present disclosure, and FIG. 3 is an exploded view of a fluid analysis cartridge, according to an embodiment of the present disclosure. FIG. 4 is a cross-sectional view of a fluid analysis cartridge cut along line I-I' of FIG. 2. Here, the terms "sample supply hole" and "second hole" may both refer to the same element indicated by 24.

As shown in FIGS. 2 to 4, the fluid analysis assembly 2 may include the fluid analysis cartridge 20.

The fluid analysis cartridge 20 may include a housing 21 that forms a support structure. The housing 21 may support the fluid analysis cartridge 20. The housing 21 may further include a holding part 21a that permits the user to hold or grasp the fluid analysis cartridge 20.

The housing 21 may have a shape to implement a particular function, and may be formed of an easy to materialize, chemically and/or biologically inactive material because the housing 21 may contact the sample. For example, the housing 21 may be formed of any of various materials including plastic materials, such as acryl, e.g., polymethylmethacrylate (PMMA), polysiloxane, e.g., polydimethylsiloxane (PDMS), polycarbonate (PC), polyethylene, e.g., linear low density polyethylene (LLDPE), low density polyethylene (LDPE), medium density polyethylene (MDPE), high density polyethylene (HDPE), polyvinyl alcohol, very low density polyethylene (VLDPE), polypropylene (PP), acrylonitrile butadiene styrene (ABS), cycloolefin copolymer (COC), etc., glass, mica, silica, semiconductor wafer, etc. However, the materials are only examples to be used as materials for the housing 21, and exemplary embodiments of the present disclosure are not limited thereto. Any material that has chemical and/or biological stability and that can be mechanically processed may be used to form the housing 21 in accordance with exemplary embodiments of the present disclosure.

The fluid analysis cartridge 20 may further include the test unit 30 in which the sample reacts with a reagent. The reagent reacting with the sample input to the sample receiver 22 may also be received in the test unit 30. The test unit 30 may be combined with the housing 21. In other words, the fluid analysis cartridge 20 may include both the test unit 30 configured to receive the reagent that reacts on the sample input to the sample receiver 22, and the sample collecting member 40. The test unit 30 and the sample collecting member 40 may both be combined with the housing 21 to be located on an extension of the direction of combination C oft the fluid analysis cartridge 20 (See FIG. 6A). In short, the test unit 30 and the sample collecting member 40 may each be combined with the housing 21 to be located in a line (See FIG. 6A).

The sample injected through the sample receiver 22 is input to the test unit 30 and the sample may be tested by reacting with a reagent in the test unit 30. The test unit 30 may include a test part 36 (FIG. 4) for receiving the reagent that reacts on the sample.

As shown in FIG. 4, the test unit 30 may have a structure in which three plates 31, 32, and 33 are connected. The three plates 31, 32, and 33 may be divided into a top plate 31, a middle plate 32, and a bottom plate 33. The top and bottom plates 31 and 33 are printed with a light shielding ink to protect the sample moving to the test part 36 from external light. Additionally, the light shielding ink can prevent errors in the measurement of optical properties in the test part 36.

The film used to form the top and bottom plates 31 and 33 of the test unit 30 may be selected from among polyethylene films, such as VLDPE, LLDPE, LDPE, MDPE, HDPE, etc., PP films, polyvinyl chloride (PVC) films, polyvinyl alcohol (PVA) films, polystyrene (PS) films, and polyethylene terephthalate (PET) films. However, these films are only examples, and any film that is chemically and biologically inactive, and also able to be mechanically processed may be used to form the top and bottom plates 31 and 33 of the test unit 30.

The middle plate 32 of the test unit 30 may be formed of a perforated sheet, unlike the top and bottom plates 31 and 33. For example, one or more of cellulose acetate, Nylon 6.6, Nylon 6.10, and Polyethersulfone may be used to form the perforated sheet that may be used for the middle plate 32. The middle plate 32 formed of the perforated sheet may serve as a vent to allow the sample to be moved within the test unit 30 without need for an extra driver. Furthermore, in a case that the sample is hydrophilic, the middle plate 32 may be coated with hydrophobic solution to prevent the sample from permeating to the inside of the middle plate 32.

The test unit 30 may be connected to the bottom of the housing 21. Specifically, the test unit 30 may be connected to the bottom part of the sample receiver 22 having the sample supply hole 24. A Pressure Sensitive Adhesive (PSA) may be used for attaching/connecting the housing 21 and the test unit 30. The PSA is capable of adhering to an object with as much pressure as acupressure at a room temperature in a short time, and being detached without causing cohesive failure, or leaving residue on the surface of the object. However, the housing 21 and the test unit 30 may be combined together not only with PSA, but also with any other double-sided adhesive. The housing 21 and the test unit 30 could also be connected via a mechanical connection, such at least one screw, a latch, a dovetail connection, or another type of mechanical coupling.

As shown in FIG. 4, test unit 30 may include an inlet 34 through which the sample that has passed through the sample supply hole 24 is input, a fluid path 35 through which the input sample moves, and the test part 36 in which the sample and a reagent react on each other.

The top, middle, and bottom plates 31, 32, and 33 may be combined using double-sided tape 37. Specifically, the top, middle, and bottom plates 31, 32, and 33 may be combined using the double-sided tape 37 adhered to both the top and bottom surfaces of the middle plate 32.

The fluid analysis cartridge 20 may further include a sample receiver 22 to receive the sample. The sample receiver 22 may be arranged in the housing 21 to receive the sample collected by the sample collecting member 40 (see FIG. 5 and FIG. 6A), as will be described later. Specifically, the sample receiver 22 may be arranged in the housing 21 to be opened on one side. A buffer solution to be mixed with the sample may be stored in the sample receiver 22. The buffer solution is not injected by the user to the sample receiver 22 but the fluid analysis cartridge 20 is provided for the user with the sample receiver 22 storing the buffer solution.

The sample receiver 22 may include a bottom surface 22a and an inclined surface 22b formed to extend at an angle from the bottom surface 22a. The sample supply hole 24 may be formed in the sample receiver 22 for the sample to flow into the test unit 30. The sample supply hole 24 may be formed in the bottom surface 22a of the sample receiver 22. The inclined surface 22b may serve as a guide to direct the sample to the sample supply hole 24 in order for the sample to be smoothly supplied to the test unit 30 through the sample supply hole 24.

The sample is directed to the sample receiver 22 to be examined or analyzed in the fluid analysis device 1, and may include a biological sample, such as blood, tissue fluid, body fluid including lymph, saliva, urine, or other types of biological material, or an environment sample for water quality control or soil management, without being limited thereto.

The sample supply hole 24 may have a circular form, without being limited thereto. The inclined surface 22b may be formed around the sample supply hole 24 to be inclined toward the sample supply hole 24. Accordingly, the sample may flow into the sample supply hole 24 along the inclined surface 22b.

At least one sample supply hole 24 may be formed in the sample receiver 22. If there are a plurality of sample supply holes 24 formed in the sample receiver 22, a plurality of different samples may be tested simultaneously in the single fluid analysis cartridge 20. Here, the plurality of different samples may be of the same kind (i.e., same type of biological sample) but may originate from different sources. Alternatively, the plurality of different samples may be of different kinds and originate from different sources. Alternatively, they may have the same kind but may be in different states.

The fluid analysis cartridge 20 may further include a first hole 23, and a second hole 24. The first and second holes 23, 24 may be formed to be linked to the sample receiver 22. In other words, the first and second holes 23 and 24 may be formed in the sample receiver 22. The first and second holes 23, 24 may be opened by the sample collecting member 40, which will be described later.

The first hole 23 may be formed in the sample receiver 22 for the sample collector 41 (also referred to as a sample collecting chamber) (see FIG. 5) of the sample collecting member 40 to be inserted thereto. More specifically, the first hole 23 may be formed in the inclined surface 22b of the sample receiver 22 for the sample collector 41 to be inserted thereto (see FIG. 4).

The second hole 24 may be formed in the bottom surface 22a of the sample receiver 22. As described above, the second hole 24 may refer to the same element as the "sample supply hole" 24.

The fluid analysis cartridge 20 may further include a first patch 25, and a second patch 26. The first and second patches 25, 26 may be attached to the sample receiver 22 to cover the first hole 23, and the second hole 24, respectively. However, exemplary embodiments may also include additional holes and additional patches. Additionally, the number of holes may be different from the number of patches.

The first patch 25 is attached to the inclined surface 22b of the sample receiver 22 to cover the first hole 23. Specifically, the first patch 25 may be attached to the sample receiver 22 to be penetrated by the sample collector 41 of the sample collecting member 40 inserted to the first hole 23.

The second patch 26 is attached to the bottom surface 22a of the sample receiver 22 to cover the second hole 24. The second hole 24 may be opened when the second patch 26 is pressed by the sample collector 41 inserted to the first hole 23.

As a precondition for use of the fluid analysis cartridge assembly 2, the second patch 26 needs to block the second hole 24 to prevent the buffer solution stored in the sample receiver 22 from leaking or being vaporized. Furthermore, the second patch 26 needs to be detached from the bottom surface 22a of the sample receiver 22 when pressed by the sample collector 41, or the tip 42 of the sample collector, of the sample collecting member 40 with more than a certain level of force. Moreover, the second patch 26 needs to be attached to the bottom surface 22a of the sample receiver 22 in a chemically stable way so that it does not influence the reaction between the buffer solution and the sample.

For example, the second patch 26 may be attached to the bottom surface 22a of the sample receiver 22 with double-sided tape to cover the second hole 24. The double-sided tape may be chemically inert.

In another example, the second patch 26 may be attached to the bottom surface 22a of the sample receiver 22 in an ultrasonic fusion method to cover the second hole 24.

In yet another example, the second patch 26 may be attached to the bottom surface 22a of the sample receiver 22 in a hotplate fusion method.

A method of attaching the second patch 26 to the bottom surface 22a of the sample receiver 22 is, however, not limited to the above-described examples. Other methods could also be used to attach the second patch 26 to the bottom surface 22a. For example, the second patch could be attached with a magnet. The first patch 25 and other components could also be attached to other components with magnets. Specifically, the fluid analysis cartridge 20 may include a metal material. In other words, a part of the fluid analysis cartridge 20 may be formed of the metal material. Therefore, the first patch 25, the second patch 26 and the other components could be attached to other components with magnets.

Figure 7A:
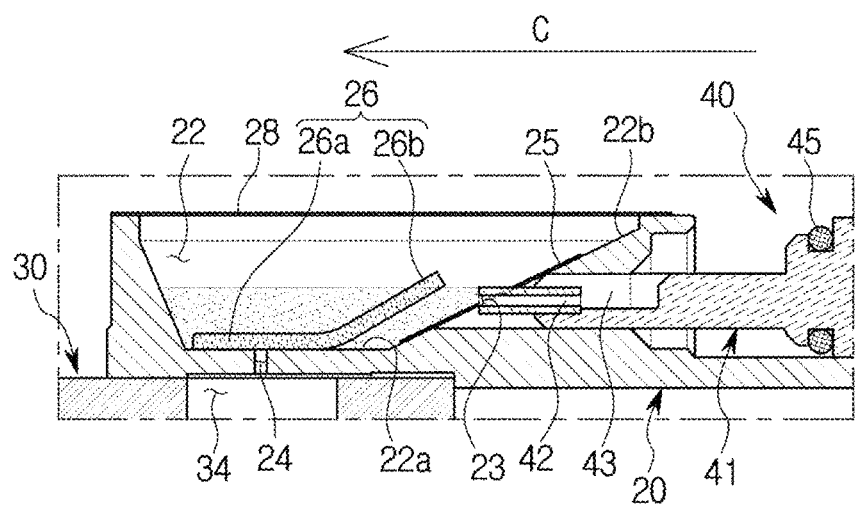
FIGS. 7A and 7B are cross-sectional views illustrating a procedure in which a sample collecting member is combined with a fluid analysis cartridge in a fluid analysis device, according to an embodiment of the present disclosure.

As shown in FIG. 7A, the second patch 26 may include an attachment part 26a to be attached to the bottom surface 22a of the sample receiver 22 to cover the second hole 24. Furthermore, the second patch 26 may include a pressed part 26b formed to extend from the attachment part 26a to be pressed by the sample collector 41 toward the test unit 30. For example, the pressed part 26b may be formed to extend from the attachment part 26a to be bent. Specifically, the pressed part 26b may be formed to extend upward in the direction of depth D, as shown in FIG. 4, of the sample receiver 22 at an angle from the attachment part 26a. From another perspective, the pressed part 26b may be formed to extend at an angle from the attachment part 26a to be pressed by the sample collector 41 to the direction of C of the sample collector 41 against the first hole 23 (FIG. 7A).

The fluid analysis cartridge 20 may further include a sealing member 28. The sealing member 28 may be combined with the housing 21 to cover an opened side of the sample receiver 22. The sealing member 28 may be comprised of a flexible material to be pressed by the pressing member 10.

Figure 5:
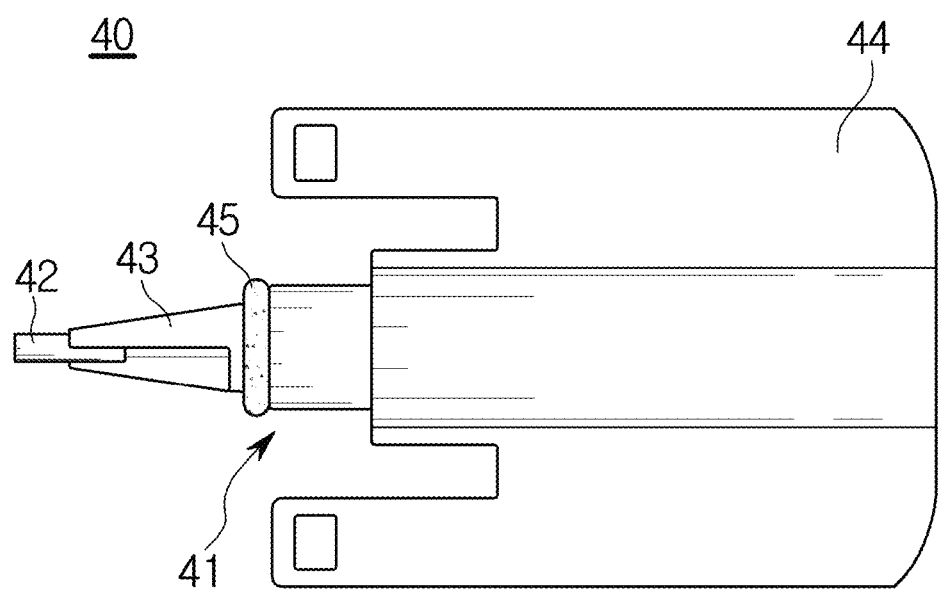
FIG. 5 shows a sample collecting member in a fluid analysis device, according to an embodiment of the present disclosure.

FIG. 5 shows a sample collecting member in a fluid analysis device, according to an embodiment of the present disclosure.

Referring to FIG. 5, the fluid analysis cartridge assembly 2 may further include the sample collecting member 40 configured to interface with the fluid analysis cartridge 20.

The sample collecting member 40 may include the sample collector 41 configured to collect a sample from an object. The sample collector 41 may include a tip 42 formed to collect a sample using capillary force. The sample collector 41 may further include a tip holding part 43 formed to hold the tip 42.

The sample collecting member 40 may further include a holder 44 formed to hold the sample collector 41.

The sample collecting member 40 may further include an O-ring 45. The O-ring 45 prevents the buffer solution and sample received in the sample receiver 22 from being leaked from the fluid analysis cartridge assembly 2 while the sample collecting member 40 is combined with the fluid analysis cartridge 20. Specifically, the O-ring 45 prevents the buffer solution and sample received in the sample receiver 22 from being leaked out through the first hole 23 by sealing the first hole 23 while the sample collector 41 is inserted to the first hole 23 (see FIG. 4). The O-ring 45 may comprise an elastic material. The O-ring 45 may be attached to the sample collector 41. Specifically, the O-ring 45 may be attached to the tip holder 43.

Since the sample collected by the sample collector 41 may be stored in the sample collecting member 40, there is no need for an extra sample container to store the sample after the sample is collected from the object with an extra collecting tool. Accordingly, a step of injecting the sample collected from the object to an extra sample container may be omitted.

Figure 6A:
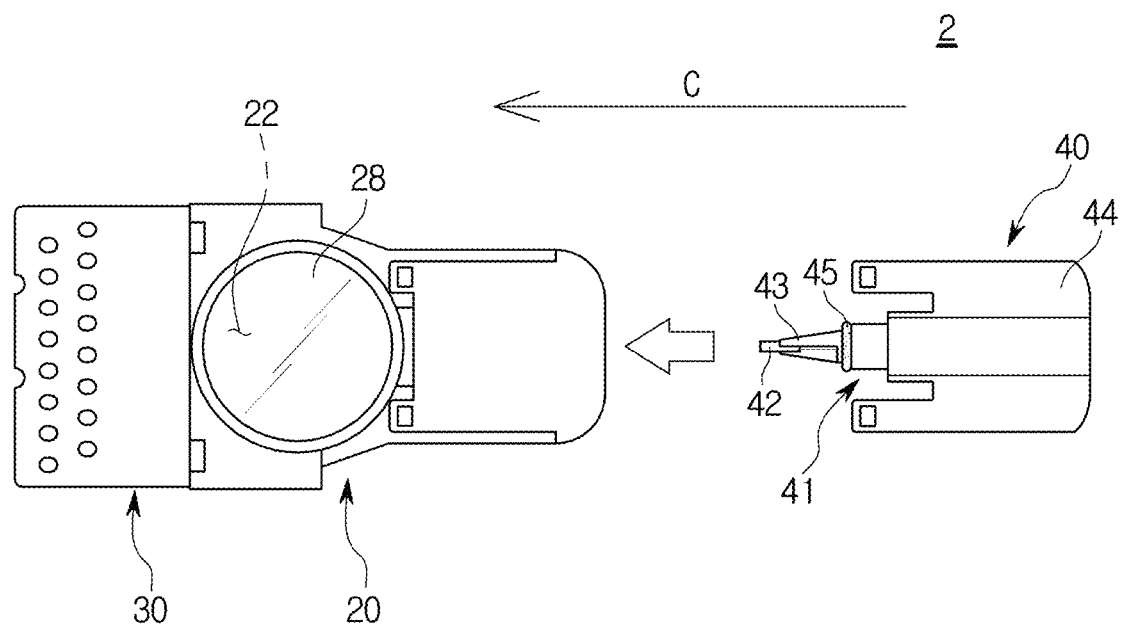
FIGS. 6A and 6B show a procedure in which a sample collecting member is combined with a fluid analysis cartridge in a fluid analysis device, according to an embodiment of the present disclosure.
Figure 6B:
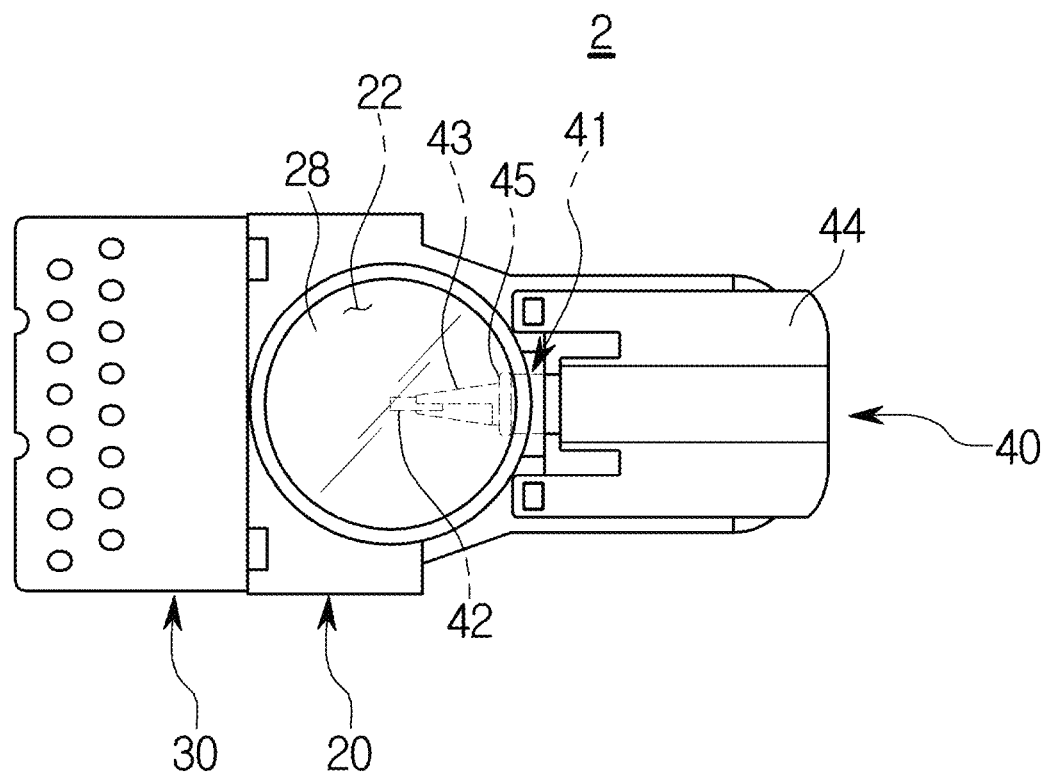
Figure 7B:
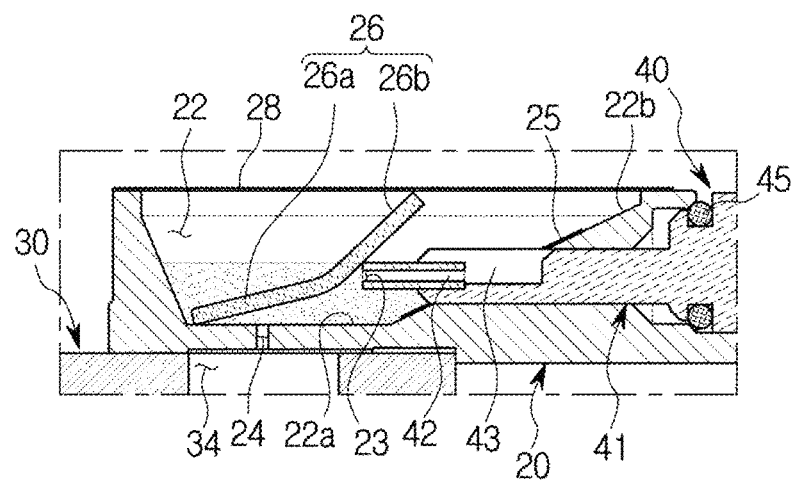

FIGS. 6A and 6B show a procedure in which a sample collecting member is connected to a fluid analysis cartridge in a fluid analysis device, according to an embodiment of the present disclosure, and FIGS. 7A and 7B are cross-sectional views illustrating a procedure in which a sample collecting member is connected to a fluid analysis cartridge in a fluid analysis device, according to an embodiment of the present disclosure. Reference numerals not shown herein may be referred to from FIGS. 1 to 5.

As shown in FIGS. 6A to 7B, the sample collecting member 40 may be connected to the fluid analysis cartridge 20.

A sample collected from an object by the sample collecting member 40 may be provided to the sample receiver 22 of the fluid analysis cartridge 20 when the sample collecting member 40 is connected to the fluid analysis cartridge 20. Specifically, the sample collector 41 of the sample collecting member 40 may be connected to the first hole 23 of the fluid analysis cartridge 20. In this process, the first patch 25 covering the first hole 23 may be penetrated by the sample collector 41. The O-ring 45 of the sample collecting member 40 may bond closely with the first hole 23 to prevent the buffer solution and sample from leaking out through a gap between the first hole 23 and the sample collector 41 inserted to the first hole 23. The second patch 26 may be pressed by the sample collector 41 in the direction of C (see FIG. 6A) of the sample collector 41 against the first hole 23. Specifically, the pressed part 26b of the second patch 26 may be pressed by the sample collector 41 in the direction of C of the sample collector 41 against the first hole 23, and as a result, the attachment part 26a of the second patch 26 may be detached from the bottom surface 22a of the sample receiver 22. Accordingly, the second hole 24 may be opened. The mixed solution of the buffer solution and sample received in the sample receiver 22 may then pass through the second hole 24 and be supplied to the test unit 30. Specifically, the mixed solution of the buffer solution and sample received in the sample receiver 22 may sequentially pass: the second hole 24, the inlet 34, the fluid path 35, and to be supplied to the test part 36. The mixed solution of the buffer solution and sample supplied to the test part 36 reacts on a reagent.

As such, connecting the sample collecting member 40 to the fluid analysis cartridge 20 may enable a sample collected by the sample collector 41 to be easily provided to the fluid analysis cartridge 20, thereby preventing the sample from being dispersed, spilled, or contaminated during the process of providing the sample to the fluid analysis cartridge 20. As shown in FIG. 7B, the fluid analysis cartridge and the sample collecting member may be configured and shaped such that when the sample collecting member 40 is inserted into the first hole, the tip 42 penetrates the first patch 25 and moves the second patch 26 to uncover the second hole.

Furthermore, since the second hole 24 linked to the test unit 30 may be opened by the sample collector 41, there is no need for an additional part that is configured to open the second hole 24. This may simplify the structure of the fluid analysis cartridge assembly 2. The manufacturing cost of the fluid analysis cartridge assembly 2 may also be reduced.

Moreover, using the fluid analysis cartridge assembly 2, which has a combined structure of the sample collecting member 40 and the fluid analysis cartridge 20, may simplify and enable a procedure of collecting and analyzing a sample, regardless of the user's skill. In other words, using the fluid analysis cartridge assembly 2, which has a combined structure of the sample collecting member 40 and the fluid analysis cartridge 20, may minimize factors that tend to cause mistakes. The system can thus decrease variations in success rates and failure rates across different users of varying skill levels. In short, even low-skilled users can conduct the tests with fewer mistakes.

Figure 8:
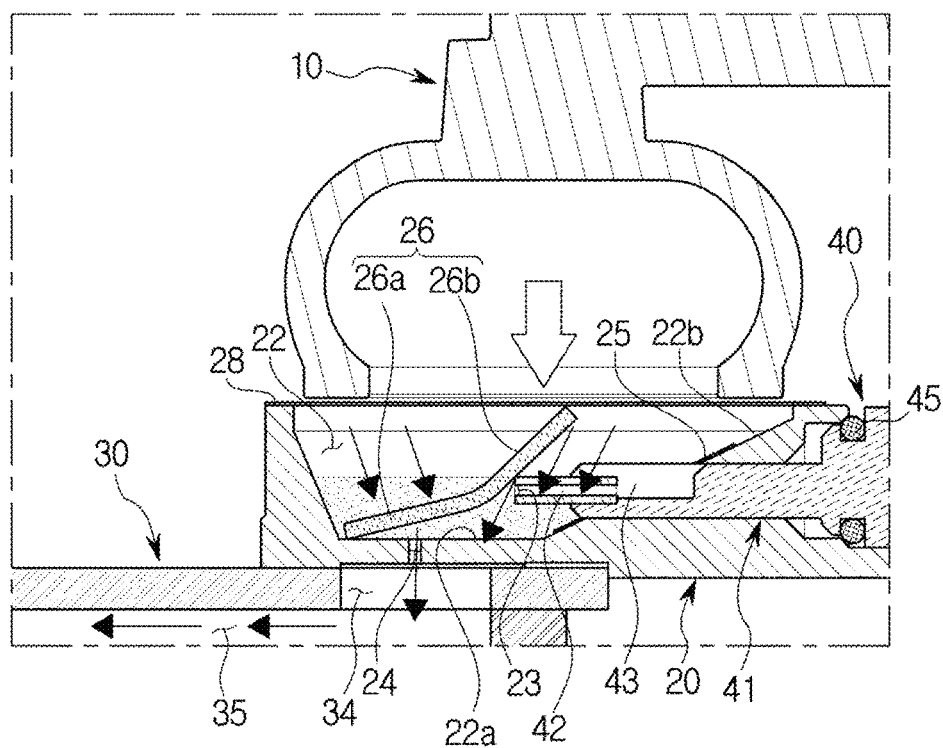
FIG. 8 is a cross-sectional view illustrating a state in which a pressing member is pressing a fluid analysis cartridge in a fluid analysis device, according to an embodiment of the present disclosure.

FIG. 8 is a cross-sectional view illustrating a state in which a pressing member is pressing a fluid analysis cartridge in a fluid analysis device, according to an embodiment of the present disclosure.

Referring to FIG. 8, the pressing member 10 may be arranged to press the fluid analysis cartridge 20 to have the sample receiver 22 shut tight, as described above.

The fluid analysis cartridge 20 may be pressed by the pressing member 10. Specifically, the sealing member 28 of the fluid analysis cartridge 20 may be pressed by the pressing member 10. While the pressing member 10 is pressing the sealing member 28, the sample receiver 22 may be in a state of high pressure. Accordingly, the mixed solution of the buffer solution and sample stored in the sample receiver 22 may then pass through the second hole 24 to the test unit 30 in a state of relatively low pressure. In other words, the mixed solution of the buffer solution and sample stored in the sample receiver 22 is pipetted to the test unit 30 from the sample receiver 22 according to the pressure difference.

Figure 9:
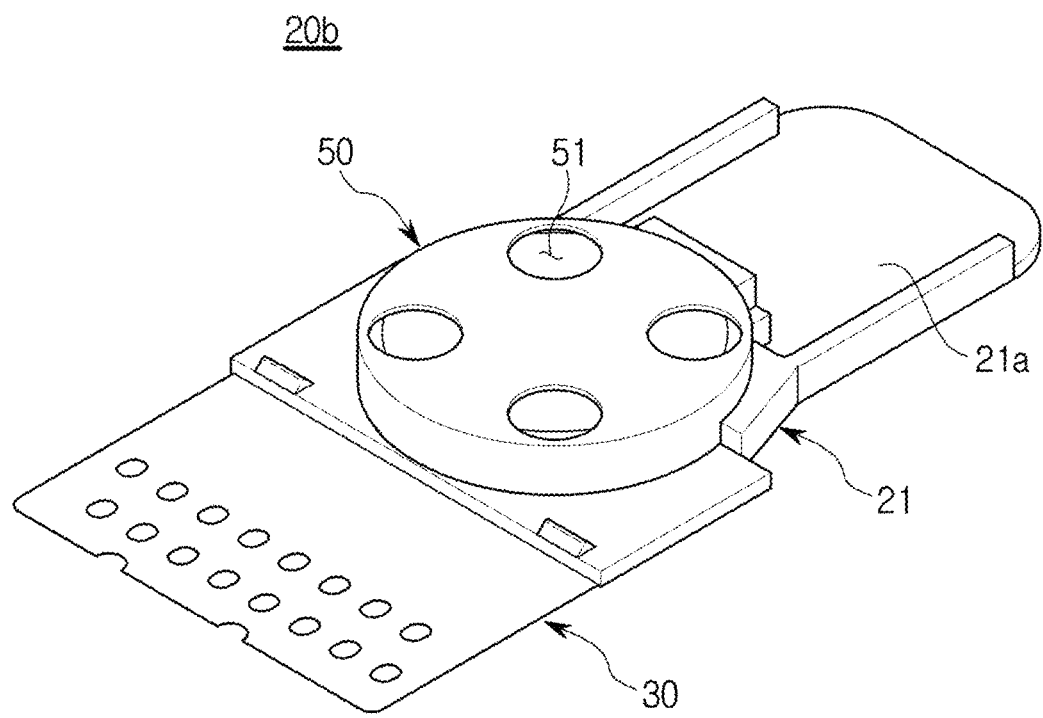
FIG. 9 is a perspective view of a fluid analysis cartridge, according to another embodiment of the present disclosure.
Figure 10:
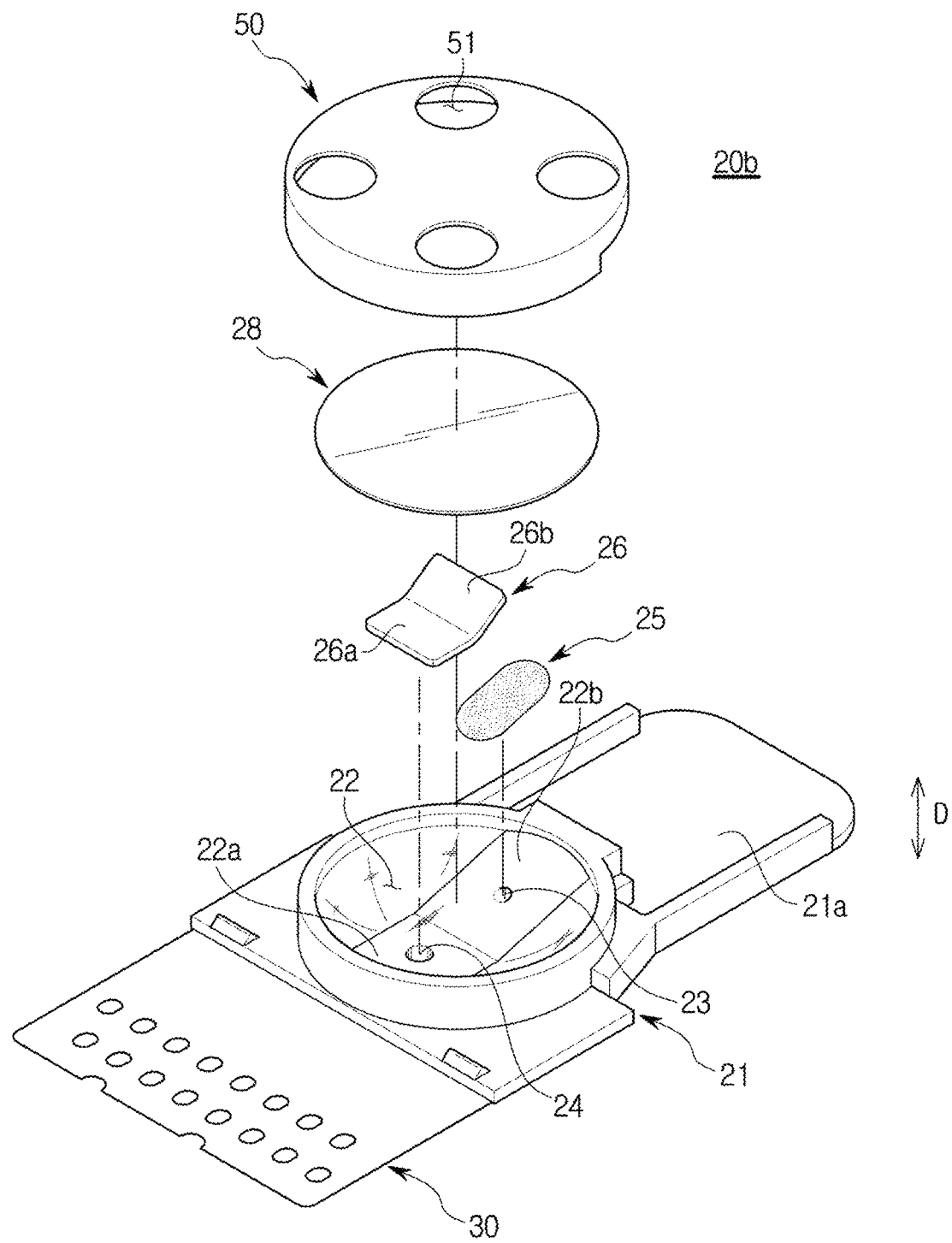
FIG. 10 is an exploded view of a fluid analysis cartridge, according to another embodiment of the present disclosure.

FIG. 9 is a perspective view of a fluid analysis cartridge, according to another embodiment of the present disclosure, and FIG. 10 is an exploded view of a fluid analysis cartridge, according to another embodiment of the present disclosure. Descriptions of elements similar to those shown in FIGS. 1 to 8 will be omitted in the following description for the sake of brevity. Reference numerals not shown in FIG. 12 may be referred to from FIGS. 1 to 8.

As shown in FIGS. 9 to 10, the fluid analysis cartridge 20b may further include a housing cover 50. The housing cover 50 may be connected to the housing 21 to cover the sample receiver 22. For example, the housing cover 50 may be connected to the housing 21 by an adhesive to cover the sample receiver 22. In another example, the housing cover 50 may be fitted into the housing 21 to cover the sample receiver 22. The mechanism for connecting the housing cover 50 is not limited to the above examples, but may be modified in other various ways. For example, the housing cover could be connected to the housing via a mechanical coupling, such as a latch.

The housing cover 50 may have a plurality of openings 51 for air ventilation. The housing cover 50 may be connected to the housing 21 to be located on an outer side of the sealing member 28. Specifically, the sample receiver 22 may be primarily covered by the sealing member 28 at one point and secondarily covered by the housing cover 50 at another point. The housing cover 50 may supplement the sealing member 28, since the sealing member 28 may be susceptible to an external force. The sealing member 28 has to be pressed by the pressing member 10 but a pressing force may occur inadvertently or as a result of some external force. To avoid such situations, the housing cover 50 may be formed of a harder or more rigid material than the sealing member 28. Alternatively, the housing cover 50 may be formed of the same material as the housing 21. For example, the housing cover 50 may be formed of a plastic material.

In an exemplary embodiment, the housing cover 50 may be integrally formed with the housing 21.

According to exemplary embodiments of the present disclosure, connecting a sample collecting member having a sample collector with a fluid analysis cartridge may enable a sample collected by the sample collecting member to be easily transferred to the fluid analysis cartridge, thereby preventing the sample from being dispersed, spilled, or contaminated during the process of transferring the sample to the fluid analysis cartridge.

A hole linked to a test unit may be simply opened by the sample collecting member combined with the fluid analysis cartridge, eliminating the need for an additional mechanical element configured to specifically open the hole.

Using a fluid analysis cartridge assembly, which has a combined structure of the sample collecting member and the fluid analysis cartridge, may simplify and enable a procedure of collecting and analyzing a sample to be easily performed regardless of the user's skill level.

Several embodiments have been described above, but a person of ordinary skill in the art will understand and appreciate that various modifications can be made without departing the scope of the present disclosure. Thus, it will be apparent to those ordinary skilled in the art that the true scope of technical protection is defined by the following claims.

What is claimed is:

1. A fluid analysis cartridge assembly comprising:
a sample collecting member having a sample collecting chamber; and
a fluid analysis cartridge configured to be connected to the sample collecting member,
wherein the fluid analysis cartridge comprises:
a housing;
a sample receiving chamber arranged in the housing and configured to receive a sample from the sample collecting chamber, wherein the sample receiving chamber stores a buffer solution to be mixed with the sample;
a first hole arranged in the housing and located on one side of the sample receiving chamber, the first hole being covered by a first patch and configured to be opened by connecting the sample collecting member to the first hole;
a test chamber coupled to the housing for receiving a reagent to react with a sample input to the sample receiving chamber; and
a second hole formed on a bottom surface of the sample receiving chamber so that the sample flows to the test chamber, and covered by a second patch attached to the bottom surface of the sample receiving chamber, and
wherein the second hole is configured to be opened when the second patch is moved by a portion of the sample collecting member being inserted into the first hole.

2. The fluid analysis cartridge assembly of claim 1, wherein the first patch is attached to the sample receiving chamber.

3. The fluid analysis cartridge assembly of claim 1, wherein the first patch is penetrated by the sample collecting chamber inserted to the first hole.

4. The fluid analysis cartridge assembly of claim 1, wherein the second patch comprises:
an attachment part attached on the bottom surface of the sample receiving chamber to cover the second hole; and
a pressed part formed to extend from the attachment part to be pressed by a portion of the sample collecting member.

5. The fluid analysis cartridge assembly of claim 4, wherein the pressed part is formed to extend from the attachment part so as to be inclined with respect to the attachment part.

6. The fluid analysis cartridge assembly of claim 1, wherein the fluid analysis cartridge further comprises:
a sealing member coupled to the housing to cover an opened side of the sample receiving chamber.

7. The fluid analysis cartridge assembly of claim 6, further comprising:
a pressing member configured to press the sealing member,
wherein the sealing member comprises a flexible material.

8. The fluid analysis cartridge assembly of claim 7, wherein the sample and buffer solution in the sample receiving chamber are arranged to flow to the test chamber according to a pressure difference between the sample receiving chamber and the test chamber that occurs as the pressing member presses the sealing member.

9. The fluid analysis cartridge assembly of claim 1, wherein the fluid analysis cartridge further comprises:
a housing cover integrally formed with the housing and having a plurality of openings for air ventilation.

10. A testing system comprising:
a fluid analysis cartridge comprising:
a sample receiving chamber, the sample receiving chamber having a first hole on a side portion and a second hole on a bottom portion; and
a first patch that covers to close the first hole, and a second patch that covers to close the second hole;
a sample collecting member comprising:
a sample receiving chamber; and
a tip portion disposed at one distal end of the sample collecting member,
wherein the fluid analysis cartridge and the sample collecting member are configured such that when the sample collecting member is inserted into the first hole, the tip portion penetrates the first patch, opens the first hole and opens the second hole.

11. The testing system according to claim 10, wherein the fluid analysis cartridge further comprises a testing chamber connected to the sample receiving chamber.

12. The testing system according to claim 10, wherein the second patch comprises an attachment part attached to the bottom portion of the sample receiving chamber, and a pressed part that is inclined with respect to the attachment part and contacts the tip portion when the sample collecting member is inserted into the first hole.

13. The testing system according to claim 10, wherein the fluid analysis cartridge further comprises:

a housing with the sample receiving chamber; and a sealing member coupled to the housing to cover an open side of the sample receiving chamber.

14. The testing system according to claim 13, further comprising:

a pressing member configured to press the sealing member, and wherein the sealing member comprises a flexible material.

15. The testing system according to claim 10, wherein the fluid analysis cartridge further comprises:

a housing with the sample receiving chamber; and a housing cover integrally formed with the housing and having a plurality of openings for air ventilation.

16. The testing system according to claim 10, wherein the first and the second patches are disposed along a direction in which the sample collecting member is inserted into the first hole.

17. The testing system according to claim 10, wherein the fluid analysis cartridge and the sample collecting member are configured such that when the sample collecting member is inserted into the first hole, the tip portion moves the second patch to uncover the second hole.

* * * * *